United States Patent [19]

Hansen et al.

[11] 4,314,824
[45] * Feb. 9, 1982

[54] PROGRAMMABLE, CONTINUOUS FLOW ANALYZER

[75] Inventors: Elo H. Hansen, Lyngby; Jaromir Ruzicka, Naerum, both of Denmark

[73] Assignee: Bifok AB, Sollentuna, Sweden

[*] Notice: The portion of the term of this patent subsequent to Sep. 23, 1997, has been disclaimed.

[21] Appl. No.: 147,331

[22] Filed: May 6, 1980

Related U.S. Application Data

[63] Continuation of Ser. No. 878,265, Feb. 16, 1978, Pat. No. 4,224,033.

[30] Foreign Application Priority Data

Feb. 16, 1977 [SE] Sweden .................................. 7701692

[51] Int. Cl.³ ................................................ G01N 1/18
[52] U.S. Cl. ................................. 23/230 R; 422/81; 422/82
[58] Field of Search .................. 23/230 R; 422/81, 82

[56] References Cited

U.S. PATENT DOCUMENTS 4,224,033 9/1980 Hansen et al. .................... 422/81 X Primary Examiner—Ronald Serwin
Attorney, Agent, or Firm—Poms, Smith, Lande & Rose

[57] ABSTRACT

Method and device for continuous flow-through analysis with a non-segmented laminar carrier flow, to which reagents are added at programmable intervals. The programming can be done by switching in various loops with valves, interchangeable connections or by composing the apparatus of different prefabricated modules to produce the desired reaction conditions.

9 Claims, 7 Drawing Figures

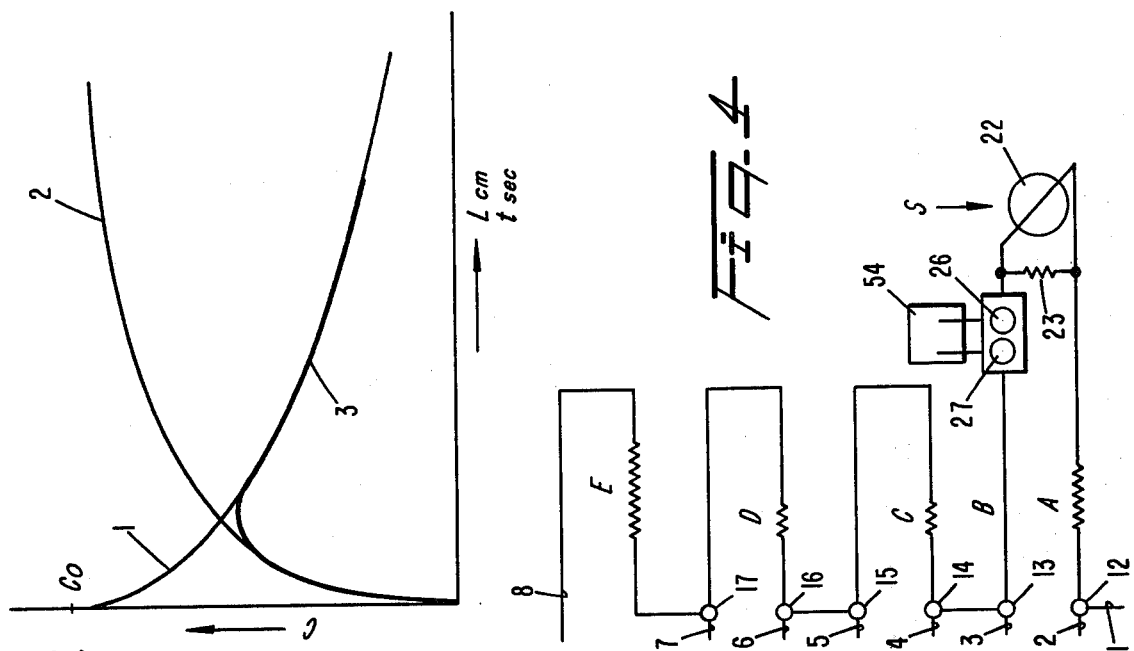
FIG. 2
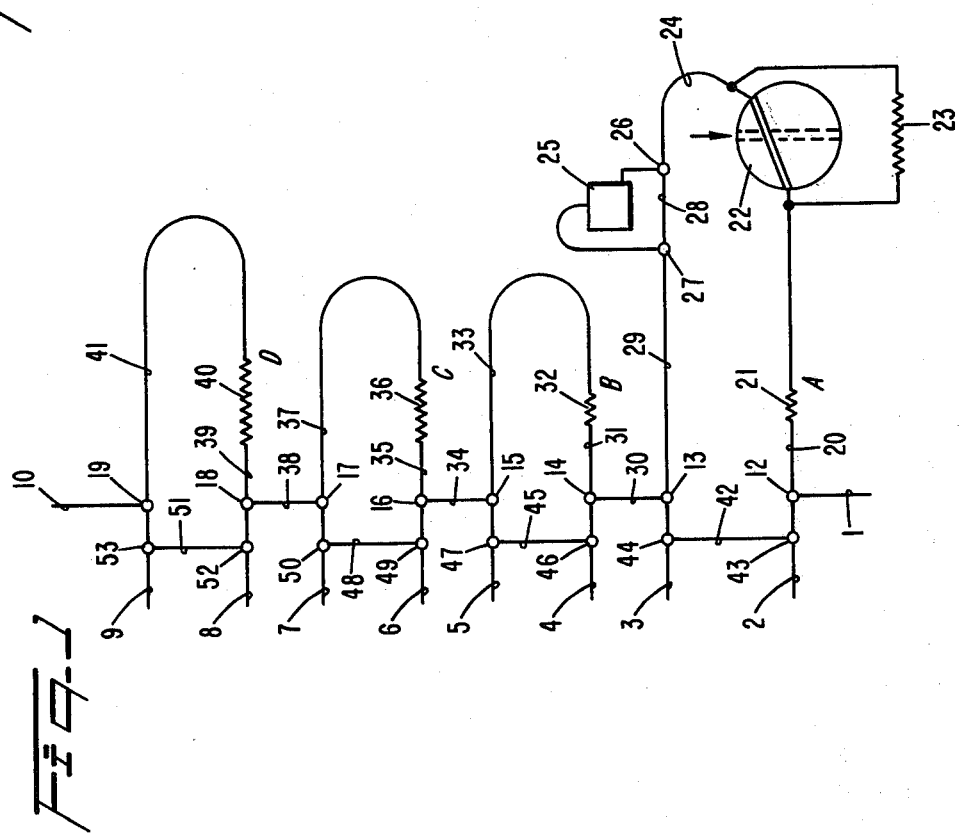
FIG. 4
FIG. 1

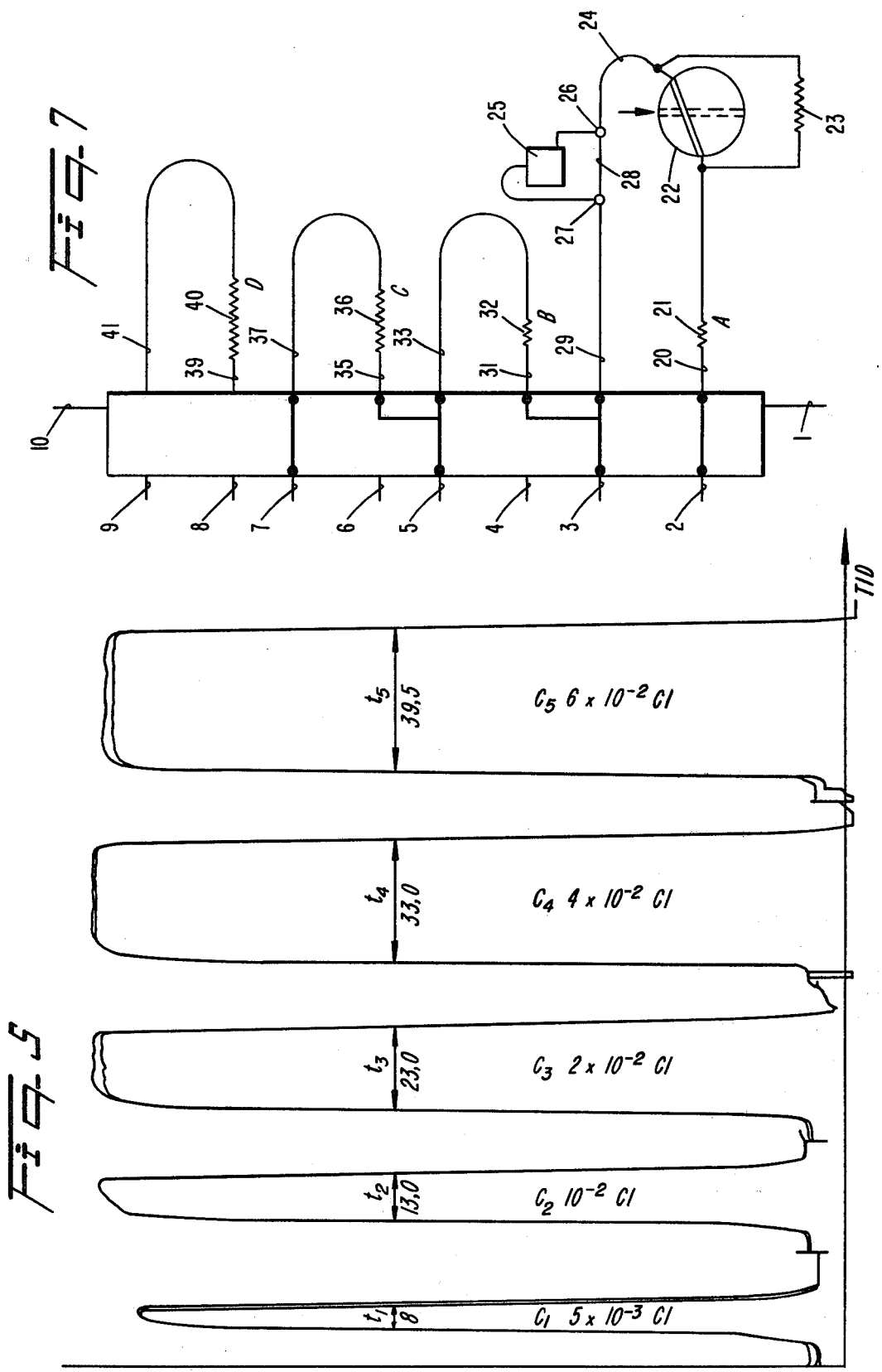

PROGRAMMABLE, CONTINUOUS FLOW ANALYZER

This is a continuation, of application Ser. No. 878,265, filed Feb. 16, 1978 now U.S. Pat. No. 4,224,033.

The present invention relates to a programmable, continuous flow analyzer with a continuous, unobstructed laminar carrier flow which is not segmented by air bubbles.

Methods of rapid, exact, chemical analysis of separate samples are very important because of the increasing need for analysis in chemical and biochemical investigations of environmental problems, food problems, clinical studies, etc. The development of methods of analysis and improving the speed of analysis are dependent on the possiblities of producing an apparatus which performs rapid and exact analyses and which has a broad range of use.

In principal, there are two different paths which have been followed in the development of apparatus for high-speed analysis. One of them involves the use of an apparatus which places each sample and the appropriate reagent in an individual container, in a manner similar to that of a laboratory technician in manual analysis. Even if this procedure has many advantages, the required apparatus is quite complicated.

The other path involves using a continuous reaction flow and provides quite rapid analysis of many different substances with relatively simple apparatus.

The greatest problem in continuous flow reaction systems has been to maintain the integrity of the samples. One of the pioneers in the field, Skeggs, Amer. J. Clin. Path, 28, 311-322, (1957), has developed a system with air bubbles between the different samples. The majority of mechanized colorimetric analyzers are now based on this system of segmentation of the reaction flow with air bubbles.

Even if the system with air segmentation is excellent at low speeds of analysis, 10-30 samples/h, it is difficult to obtain reference readings at higher speeds, 60-120 samples/h, and poor analytical accuracy is obtained.

The basic principles and characteristics of automatic analyzers are given in more detail in our U.S. Pat. No. 4,177,677, which is especially directed to supplying samples to a continuous carrier flow.

In the apparatus produced according to our earlier abovementioned patent application, the problems with dispersion of the samples has been solved, so that different analyses produce comparable results. However, a remaining problem which is closely associated with the dispersion problem is the supplying of two or more converging flows to a reaction system, and at the same time making optimal reaction conditions possible in connection with the addition of the reagents.

These problems are solved by the present invention, which makes it possible to add two or more different flows so that they become confluent and to vary the length of a main conduit during operation by switching in or switching out different conduit segments arbitrarily or according to need.

The invention will be described in more detail below in connection with examples and with the accompanying drawings.

BRIEF DESCRIPTION OF THE DRAWINGS

The drawings show in

FIG. 1 a flow chart for the apparatus according to the invention,

FIG. 2 the graph of the dispersion of a sample zone,

FIG. 4 a flow chart for another apparatus according to the invention,

FIG. 5 graph of acid titration with high dispersion,

FIG. 6 nitrogen determination at medium dispersion, and in

FIG. 7 a schematic drawing of the apparatus according to the invention constructed with modules.

FIG. 1 shows a schematic flow chart for a apparatus according to the invention in a simplified form. The reference numerals 1-10 represent a number of input or output conduits to valves or cocks 12-19, which for the sake of simplicity are shown as three-way valves. A number of loops A-D of different lengths are connected to these valves together with apparatus.

Figure 3:
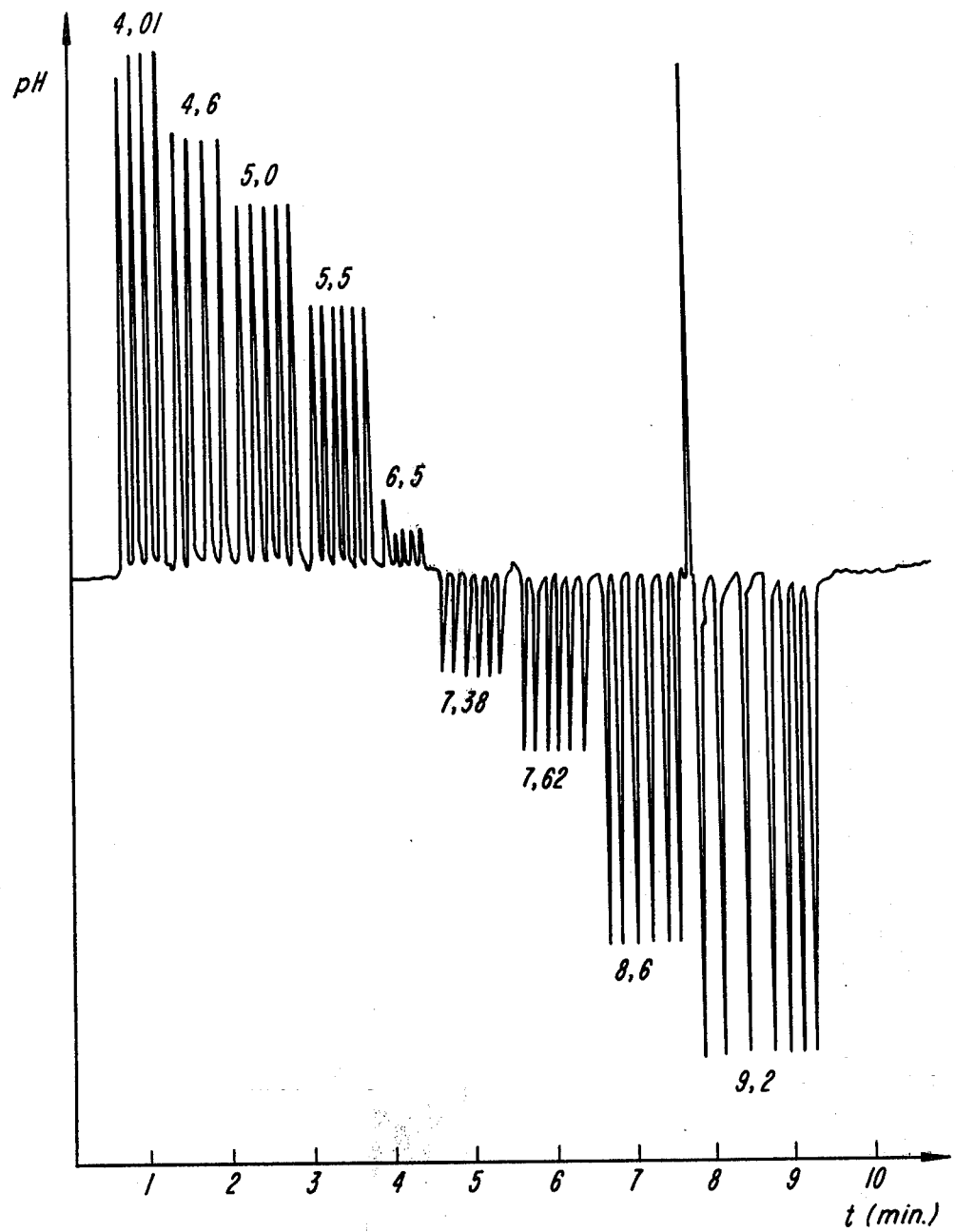
FIG. 3 a graph showing pH measurement at low dispersion.

Thus loop A consists of a conduit 20 from valve 12 to a coil 21 and from there to a sample injection device 22 with a shunting circuit 23. As desired, the valve 12 can join the loop A to conduit 1 or 2 or with both of these conduits at the same time. The sample injection device is described in detail in our Swedish Patent Application No. 7610110-4.

From the sample injection the conduit 24 continues to a back mix 25 coupled between three-way valves 26 and 27 and with a shunting circuit 28 between the valves enabling the back mix to be switched in and out as desired. From valve 27 the conduit 29 continues to valve 13 to be coupled there either to conduit 3 or via a connecting conduit 30 to valve 14 or is entirely closed off.

Valve 14 connects conduit 30 with conduit 4 or with loop B via conduit 31 or with both of these conduits. The conduit 31 goes to the coil 32, and from there conduit 33 continues to valve 15. In the same manner, loop C, 35,36,37, is connected between valves 16 and 17 and loop D, 39,40,41 between valves 18 and 19.

In a similar manner conduits 2 and 3 or valves 12 and 13 can be joined to one another via conduit 42 and valves 43 and 44, i.e. by-passing loop A. Conduits 4 and 5 can be coupled together with the connecting conduit 45 and valves 46 and 47; conduits 6 and 7 with connecting conduit 48 and valves 49 and 50; and conduits 8 and 9 with connecting conduit 51 and valves 52 and 53.

Thus in the apparatus shown a carrier flow can be supplied through, for example, conduit 1, possibly mixing it with a supplementary carrier flow via conduit 2. It then passes the coil 21 to even out the flow, is mixed with a sample solution in the sample injection device 22, is titrated in the back mix 5, is led to the outlet via conduit 3 or continues through one or more of the loops B,C and D and is thereby mixed with different reagents via one or more of the conduits 3-9 and is finally led to a measuring instrument, a colorimeter, a measuring electrode, etc. via conduit 10.

Other apparatus, instruments or loops can likewise be coupled in between two of the conduits 3-9 or the flowing solution can be taken out through one of the conduits as desired for special purposes. The flow can also be directed in the other direction adding the reagent via one or more of the conduits 3-10 and having the outlet for measurement through conduit 1 or 2.

The number of possible variations is quite large, and the examples given above are in no way exhaustive.

The procedure in several different analyses will be described in the following examples, in which loops A,B,C and D had lengths of 80, 20, 60 and 80 cm respectively and are kept at a temperature of 38° C. by thermostated baths. All of the conduits had a diameter of 0.5 mm and the connecting conduits 42,45,48 and 51 were switched out with the respective valves.

EXAMPLE 1

Chloride determination.
Programming.
Conduit 1 closed.
Conduit 2 addition of 1.5 ml/min. of a solution containing per liter 15% ethanol in water: 0.626 g mercury(II)thiocyanate, 30 g iron(III)nitrate and 4.7 g nitric acid, 26,28,27 back mix switched out.
Conduits 3 and 4 closed.
Conduit 5 coupled to flow-through cell, 10 mm, volume 18 μl (microliters), for measurement at 480 nm.
Conduits 6-10 closed.
With a sample volume of 30 μl a usable measuring range of 0.5-20 ppm Cl was obtained, and with a sample volume of 10 μl a usable measuring range of 10-50 ppm Cl was obtained.

EXAMPLE 2

Ammonia determination.
Programming.
Conduit 1 closed.
Conduit 2 addition of 1 ml water/min. 26,28,27 back-mix switched out.
Conduit 3 addition of 1 ml/min. of a solution containing per liter 33% ethanol in water: 50 g phenol and 120 g NaOH.
Conduit 4 closed.
Conduit 5 addition of 1 ml/min. of a solution of 4% $Cl_2$ in water and containing per liter 20 g NaOH and 20 g borax.
Conduit 6 closed and conduit 7 coupled to a flow-through cell, 10 mm long, volume 18 μl for measurement at 620 nm.
Conduits 8-10 closed.
Sample volume 30 μl and usable measuring range 1.0-25 ppm $NH_3$.

EXAMPLE 3

Determination of pCa in serum.
Programming.
Conduit 1 closed, conduit 2, 3.0 ml/min 0.14 N NaCl and 26,28,27 back mix switched out. Conduit 3 coupled to flow-through cell with calcium electrode and conduits 4-10 closed.
Sample volume 30 μl and usable measuring range $5 \times 10^{-4} - 5 \times 10^{-3}$ M $Ca^{2+}$ (pCa 2.7-3.7).

For the sake of illustration, in these examples the outlet for measurements was made at different points, but the usual case is that a measuring instrument or a measuring cell is permanently coupled in at 10 and that the fluid flow for measurement is conducted there by making connections between the existing conduits. For the sake of clarity, in FIG. 1 the valves are shown as three-way valves, for example valves 46 and 14 in conduit 4. In practice a single valve is used instead of the two valves and it can be electrically controlled so that the entire programming is done from a clearly arranged control panel where the flow paths are set and controlled directly. Likewise, the valves or interchangeable connections can be made with several functions so that various loops are coupled in parallel between two valves and the loop desired at that particular time can be switched in by the programming on the control panel.

The dispersion of the sample plug in the carrier solution is of vital interest in analysis according to the invention, and the analysis apparatus according to the invention can be programmed to produce different degrees of dispersion. At low dispersion of the sample plug the dilution at the front and rear edges of the plug will be minimal and the gradient curve will thus be quite steep, while a high dispersion produces a gentle gradient curve. The degree of dispersion is determined by the velocity of the flow, the length and inner diameter of the loops, and different effects in analysis are obtained by programming for different degrees of dispersion.

The dispersion of the sample zone in a tube with laminar flow follows the formula $$\frac{C}{C_{max}} = \left(\frac{L}{1_s}\right)^{N-1} \frac{1}{(N-1)!} e^{-L/1_s} \qquad (1)$$

in which C designates the sample concentration, L is the length of the reactor loop and N and $1_s$ are constants of the system.

The formation of the colored product of a chemical reaction is often a case of first order kinetics where for a certain pumping speed the following relationship is valid:

$$C/C_{max} = 1 - e^{-kL} \qquad (2)$$

where k is a constant.

Thus, in the simple case where N=, Equation (1) is depicted by curve (1) in FIG. 2, while Equation (2) is represented by curve (2) in the same figure. The resulting curve (3) is then a characteristic for each flow system where it can be obtained by injecting the same sample and varying either L or the pumping speed.

The number N is, in fact, the number of theoretical mixing chambers. In the automatic titration procedure special advantage is taken of the case where N=L and k is very large (instant reaction); here a relatively large mixing chamber serves as the chemical reactor. We will return to the theories behind this in connection with the following examples.

These examples were carried out with an apparatus according to FIG. 3, in which the corresponding numerals and letters have the same meanings as in FIG. 1 and with the following dimensions for the loops: A 60 cm, 0.5 mm, B 20 cm, 0.5 mm, C 30 cm, 0.75 mm, D 30 cm, 0.75 mm and E 60 cm, 0.75 mm. 54 designates a flow-through cell of the type described in Swedish Patent Application No. 7610221-9 and is coupled in between 26 and 27.

EXAMPLE 4

Low dispersion.
Measurement of pH with glass electrode in flow-through cell.
Measuring range ca 5 pH units, sample volume 30 μl and analysis rate 475 samples/h.
Programming.
Conduit 1 closed, conduit 2 reagent inlet, 3.0 ml/min. and conduit 3 outlet, 4.0 ml/min. Conduits 4-8 closed, 26,27 coupled to a flow-through cell for measurement with glass electrode. By using a special electrode design according to our Swedish Patent Application No. 761221-9 with the solution flowing over the surface of the electrode, the outflowing amount will be greater than the inflowing.

As a reagent a buffer solution with pH 6.70 was used with a composition $1.0 \times 10^{-3}$ M $Na_2HPO_4$, $1.0 \times 10^{-3}$ M $NaH_2PO_4$, $1.0 \times 10^{-1}$ M NaCl. The composition of the reagent solution is suitably selected so that its pH lies in the middle of the pH values of the samples.

Measurements on 9 standard buffer solutions in the pH range 4.6-9.2 are shown in FIG. 3 with 4-6 different measurements of each solution. The accuracy can be seen by the agreement of the height of the peaks.

EXAMPLE 5

High sample dispersion. A strong acid is titrated with a strong base.

Programming.

Conduit 1 closed, conduit 2 addition of 1.3 ml/min. $5 \times 10^{-3}$ M NaOH containing per 500 ml;: 1 ml indicator consisting of 0.4 g Bromothymol Blue, 25 ml 96% ethanol and distilled water to 100 ml. Conduit 3 is coupled to a flow-through cell, 10 mm, 18 $\mu$l for measurement at 620 nm. Conduits 4-10 closed, 26-27 open to the mixing chamber at 1 ml and containing a magnetic stirrer, so that an effective agitation in the mixing chamber is obtained when placed on a magnetic stirring table.

The sample volume was 200 $\mu$l, and standard solutions of diluted hydrochloric acid were produced by successive dilution of a base solution with distilled water. The measurements were done at room temperature, and the usuable measurement range was $2 \times 10^{-2}$ M-$5 \times 10^{-1}$ M or the equivalent amount of another strong acid.

The quantitative determination of the acid concentration by titration of the acid HCl with the base NaOH is done by the acid samples being injected in a flow-through system according to FIG. 4, in which a dilution gradient is created in the mixing chamber, cf. FIG. 2, curve (1). As a reagent flow a $1.0 \times 10^{-3}$ M NaOH solution was used containing the indicator Bromothymol Blue. Through injection of an acid sample of sufficiently high concentration, the indicator in the mixing chamber changes to yellow, but the acid sample is then gradually diluted by the continuous pumping in of carrier solution and when its concentration is less that that of the carrier flow, a second color change occurs to the blue basic color, i.e. the change of color marks the point of equivalence, and the time between the two changes in color discloses the concentration of the acid. The monitoring for the actual color change is continuous via a flow-through cell mounted in a spectrophotometer and set to a wavelength of 620 nm.

Provided that the injected sample is added to the mixing chamber as a pulse and then assumed to be mixed homogeneously with the carrier flow before it begins to exit from the chamber, it can be shown mathematically that the dilution gradient follows the equation $$C_t = C_o e^{-vt/V} \qquad (3)$$

where $C_t$ is the concentration of the acid at time t, $C_o$ the concentration at time o, i.e. when the entire sample is still inside the chamber, v is the speed of the pump in ml/min, t the time in minutes and V the volume of the mixing chamber in ml.

After taking logarithms and converting to base-10 logarithms, the equation (3) can also be written $$\log C_t = \log C_o - tv/(V \ln 10) \qquad (4)$$

or $$t = (V/v \ln 10 \log C_o - (V/v) \ln 10 \log C \qquad (5)$$

When an acid pulse is injected in the basic carrier flow, and provided that the acid-base reaction occurs instantaneously, the point of equivalence is reached after a time $t_{eq}$ at which $\log C_{HCl} = \log C_{NaOH} = \log C$, i.e.

$$t_{eq} = (V/v) \ln 10 \log C_o - (V/v) \ln 10 \log C_{NaOH} \qquad (6)$$

that is to say the last term is a constant. A graph mapping of $t_{eq}$ against $\log C_o$, based on a series of acid standards, produces a straight line with the slope $V/v \ln 10$, and from this calibration curve it is possible by measuring $t_{eq}$ in a given sample to determine its initial concentration $C'_o$.

In Equation (6) $C_o$ is, as was stated earlier, the concentration in the mixing chamber, but when the sample volume is held constant, in this case 200 $\mu$l, the diagram can be read instead $C'_o$ = initial concentration of sample.

Extrapolated to $t_{eq} = 0$, the equation can be reduced to $\log C_o = \log C_{NaOH}$, i.e. the value of $\log C_{NaOH}$ is directly reflected in the sensitivity limit of the process.

FIG. 5 shows the graphed results. The time t has been marked for each sample, and it is proportional to the width of the peak in mm and to the logarithm of the concentration in the sample. The color of the solution is blue in the lower portion of the curve and yellow in the upper portion.

EXAMPLE 6

High sample dispersion.

A strong acid is titrated with a strong base.

A controlled concentration gradient of the injected acid sample is obtained and the sample is then mixed continuously with a solution of a base containing an acid-base indicator whose color can be measured continuously. The range of measurement is about 0.8 of the concentration decade. The quantative evaluation is made as previously by measuring the half-width of the registered signal, which is proportional to the logarithm of the concentration. The relative position of the range of measurement is a function of the molarity of the reagent solution, so that for example a $10^{-3}$ M NaOH solution gives a range of measurement of about $4 \times 10^{-3} - 2 \times 10^{-2}$ M $H^+$.

The sample volume was 30 $\mu$l and the greatest measuring speed was 60 samples/h.

Programming for the same apparatus as in Example 4.

Conduit 1 closed, conduit 2 distilled water 1.66 ml/min. and conduit 3 closed. Conduit 4 reagent addition 1.66 ml/min., conduits 5-6 closed and conduit 7 open to the flow-through cell. Conduit 8 closed and 26-27 open to a gradient tube with length 25 cm and inner diameter 1.70 mm.

Reagent solution: Diluted sodium chloride containing per 500 ml: 1 ml indicator consisting of 0.4 g Bromothymol Blue, 25 ml 96% ethanol and distilled water to 100 ml.

Standard solutions with diluted hydrochloric acid were prepared by successive dilution of a main solution with distilled water. The measurements were done at 620 nm and at room temperature.

According to the flow chart on FIG. 4 distilled water enters through 2, passes through the loop A to the sample injection 22, from there to 26 and through the gradient tube to 27, through the loop E to 4 where the reagent solution is added and then through C and D and out through 7 to the measuring cell.

Between the low and the high degrees of dispersion there is a large range of use with medium dispersion of the sample plug.

EXAMPLE 7

Medium-dispersion.

Measurement of Kjedahl nitrogen.

Ammonia is oxidized with hypochlorite to chloramine, which then reacts with phenol to Indolphenol Blue whose color intensity is measured colorimetrically. The range of measurement is 1–3.5% N, where %N refers to the percentage of dry vegetable matter fused according to the usual Kjedahl method with 300 mg vegetable matter in a final volume of 50 ml with the acidity of 1.0 M sulfuric acid. It is important that air be removed from the alkaline reagent solution before use, for example in an Erlenmeyer flask with a water jet pump. Furthermore the flasks should be protected from the atmosphere to prevent absorption of carbon dioxide.

The sample volume is 30 $\mu$l, the maximum speed is 90 samples per hour and the highest sensitivity is 0.75% N.

Programming.

Conduit 1 closed, conduit 2 addition of reagent 1 at 1.66 ml/min, and conduits 3–5 closed. Conduit 6 addition of reagent 2 at 1.23 ml/min., conduit 7 closed, conduit 8 open to the flow-through cell, 26,27 closed.

Reagent 1 was made up of 25.0 g phenol, 60.0 g sodium hydroxide, 150 ml 96% ethanol and distilled water to 1.0 liter. Reagent 2 consisted of 20.0 g sodium hydroxide, 20.0 g borax, 800 ml bleaching solution containing 5% active chlorine and distilled water to 1.0 liter. Standard solutions were prepared by diluting an ammonium sulphate solution with 8% N with diluted sulfuric acid.

Figure 6:
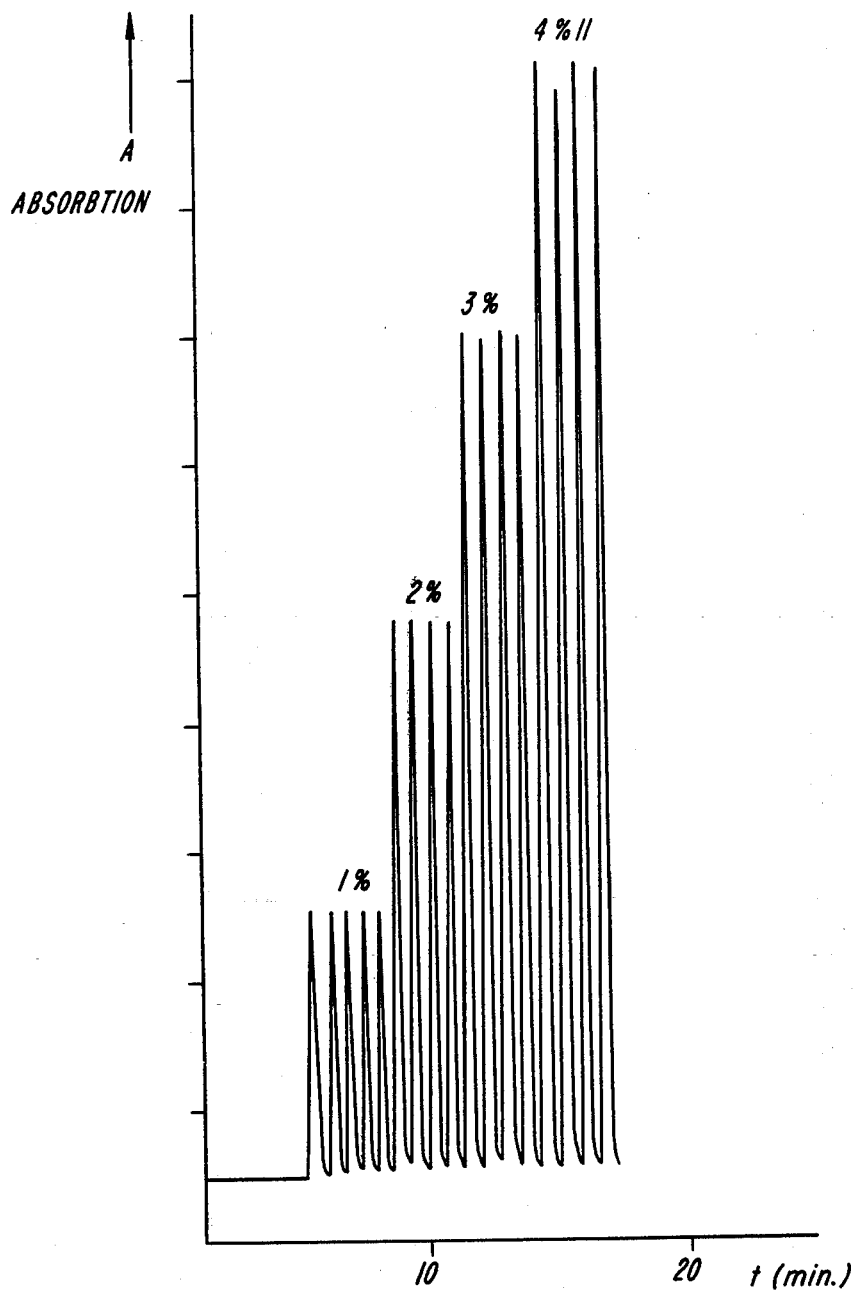

The measurements were taken at a temperature of 34° C. at 620 nm in a measuring cell with a 10 mm optical path and volume 18 $\mu$l. The graph of the results is given in FIG. 6.

As is evident from the above, the analysis apparatus according to the invention has a very wide range of use. The sample amounts required are quite small, in some cases less than 10 $\mu$l, even though as a rule sample quantities of 20–30 $\mu$l are used. However, there is no obstacle to the use of larger sample quantities of 60–70 $\mu$l and up to 100 $\mu$l or even several hundred $\mu$l. The dimensions of the loops and the conduits must be dependent on the sample quantities used so that the flow rate will be sufficiently low to prevent undesirable turbalence, i.e. a sufficiently low Reynolds number to maintain the desired degree of dispersion in each case. Reynolds numbers below 500 are usually suitable, and numbers in the range 10–150 have been used with success. In certain cases a Reynolds number as low as 2 has been used. When analyzing organic samples, the viscosity can be appreciably greater than for ordinary simple inorganic acids or bases, and the flow conditions must then be changed, of course.

The diameter of the conduits is also of importance for the flow and for small samples we have found a diameter of 0.25 mm to be about right even though we have used smaller diameters, 0.10 or the like. But with larger sample quantities a larger diameter must be used, such as 0.5 mm, 1.0 mm and even greater. In the gradient tube according to Example 6, a diameter of 1.7 mm is used and even larger diameters can be used.

The flexibility of the apparatus can, as has already been mentioned, be made quite high by coupling various loops in parallel between the valves and the desired loop can be switched in or out by a simple valve operation or by replacing an interchangeable connection. We have, however, also used with success a construction in which loops cast in a plastic block or coupled to a plastic block are inserted in a socket, thus connecting them sealingly into the system. In this way simple three-way valves at positions 12-19 can make the valves 43,44,46,67 etc. unnecessary, while preserving the same coupling possibilities, but with unlimited flexibility. A coupling with the more extensive valve system is suitable when a limited number of different types of analyses are to be done, while for research purposes or for the development of new methods, the latter method with insertable loops, provides unlimited variations at very low cost.

When only a few types of standard analyses are required, it can be advantageous to replace all of the valves with programmed gauge blocks or cassettes, of plastic for example, which directly block all of the undesired connections, and which connect those points which are to be connected for the analysis in question by interchangeable connections.

FIG. 7 shows an embodiment with such a cassette inserted for ammonia determination according to Example 2. This cassette fulfills the same functions as the valves shown in FIG. 1, and has the advantage of preventing misprogramming. The seal at the connections is in itself quite sufficient, with ordinary slide fitting between the plastic surfaces, but the cassettes can also be provided with cut grooves and inserted gaskets around the openings.

Likewise, an arbitray number of valves can be arranged in the cassettes. Thus all of the valve functions shown in FIG. 1 can be housed in a cassette even if valves are entirely avoided in most cases when using cassettes for programming, or possibly with one or two valves.

What we claim is:

1. A method of preparing a sample for treatment in which a continuous flow of liquid carrier receives sample portions, said method comprising: passing said carrier through a conduit in a manner such that flow of said carrier is laminar, unsegmented and continuous, introducing sample portions into said carrier, controlling dispersion of said sample portion in said carrier by varying at least one of the following: the volume of said sample portion, the flow velocity of said carrier, or the dimensions of said conduit conducting said sample and said carrier.

2. The method of claim 1 wherein dispersion of said sample portion and said carrier is controlled by varying the length of the conduit through which said sample and said carrier is passed.

3. The method of claim 1 wherein dispersion of said sample portion and said carrier is controlled by varying the diameter of said conduit.

4. The method of claim 1 wherein dispersion of said sample portion and said carrier is controlled by varying the volume of said sample.

5. A method of treating a sample in which a continuous flow of a liquid carrier receives sample portions, said method comprising: passing said carrier through a conduit in a manner such that flow of said carrier is laminar, unsegmented and continuous, controlling dispersion of said sample portions in said carrier by varying at least one of the following: the volume of said sample portion, the flow velocity of said carrier, the dimensions of said conduit conducting said sample and said carrier; and introducing a treatment material into said sample as it is carried through said conduit.

6. The method of claim 5 wherein the treatment material is a reagent which chemically reacts with said sample.

7. An apparatus for continuous flowthrough treatment of samples comprising:
a main conduit for conducting a liquid carrier, said conduit being disposed to conduct said carrier in a manner such that the flow of said carrier is laminar, unsegmented and continuous, means for inserting sample plugs into said carrier at controlled intervals, and means for controlling the dispersion of said sample plugs in said carrier.

8. An apparatus for continuous flowthrough treatment of a sample comprising:
a main conduit for conducting a liquid carrier, said conduit being disposed to conduct said carrier in a manner such that the flow of said carrier is laminar, unsegmented and continuous; means for inserting sample plugs into said carrier at controlled intervals; means for introducing a treatment material into said carrier; and means for controlling the dispersion of said sample plugs in said carrier.

9. The method of claim 1 wherein dispersion of said sample portion and said carrier is controlled by varying the flow velocity of said carrier.

* * * * *